(12) United States Patent
Spencer

(10) Patent No.: US 6,979,327 B2
(45) Date of Patent: Dec. 27, 2005

(54) TREATMENT OF VITILIGO

(75) Inventor: James M. Spencer, St. Petersburg, FL (US)

(73) Assignee: Mount Sinai School of Medicine, New York, NY (US)

(*) Notice: Subject to any disclaimer, the term of this patent is extended or adjusted under 35 U.S.C. 154(b) by 0 days.

(21) Appl. No.: 09/790,786

(22) Filed: Feb. 22, 2001

(65) Prior Publication Data

US 2002/0013609 A1 Jan. 31, 2002

Related U.S. Application Data

(60) Provisional application No. 60/184,971, filed on Feb. 25, 2000.

(51) Int. Cl.[7] .............................................. A61B 18/18
(52) U.S. Cl. ................................ 606/9; 606/3; 607/88; 607/89; 607/94; 128/898
(58) Field of Search .................. 606/3, 9, 2; 607/88–91, 607/94; 128/898, 897

(56) References Cited

U.S. PATENT DOCUMENTS

| | | | |
|---|---|---|---|
| 4,103,175 A | | 7/1978 | Levin |
| 4,558,700 A | | 12/1985 | Mutzhas |
| 4,674,507 A | | 6/1987 | Basso |
| 5,217,455 A | | 6/1993 | Tan |
| 5,312,395 A | * | 5/1994 | Tan et al. ...................... 606/9 |
| 5,433,942 A | * | 7/1995 | Wood et al. .................. 424/59 |
| 6,017,360 A | * | 1/2000 | Chubb et al. ................. 607/88 |
| 6,323,219 B1 | * | 11/2001 | Costanzo ..................... 514/317 |
| 6,413,268 B1 | * | 7/2002 | Hartman ....................... 607/94 |
| 6,436,127 B1 | * | 8/2002 | Anderson et al. ............. 607/89 |
| 2003/0113540 A1 | * | 6/2003 | Anderson et al. ........... 428/403 |

OTHER PUBLICATIONS

T.M. Lotti et al. "UV–B radiation microphototherapy. An elective treatment for segmental vitiligo." J Eur. Acad. Dermatol. Venereol. 13 (1999) 102–I 08.*

Bossuyt et al., "The Development of Guidelines for the Treatment of Vitiligo," Arch Dermatol, vol. 135, Dec. 1999.*

Westerhof et al., "Treatment of Generalized Vitiligo in Children with Narrow–band (TL–01) UVB Radiation Therapy,"J Am Acad Dermatol, vol. 42, 2, pp 245–253, Feb. 2000.*

Asawanonda P., Anderson R., Chang Y., Taylor CR., "308–nm Excimer laser for the treatment of psoriasis" A dose response study, Arch Dermatol 2000; 136:619–624.

Elliott, J., "Clinical experiences with methosxalen in the treatment of vitiligo," J. invest Dermatol (1959), 32:311–14.

Farah F., Kurban A., Chaglassian H., "The treatment of vitiligo with psoralens and triamcinolone by mouth," Br J Bermatol (1967), 79–89–91.

(Continued)

Primary Examiner—A. Farah
(74) Attorney, Agent, or Firm—Darby & Darby

(57) ABSTRACT

Disclosed herein is a novel method of treating vitiligo by using an excimer laser that emits light in the UVB range. The invention includes a method of incrementally increasing exposure of affected vitiligo areas with UVB laser light from an excimer laser to restore pigmentation to skin areas afflicted with vitiligo.

19 Claims, 7 Drawing Sheets

(6 of 7 Drawing Sheet(s) Filed in Color)

OTHER PUBLICATIONS

Njoo MD., Bos JD., Westerhof W., "Treatment of generalized vitiligo in children with narrow–band (TL–01) UVB radiation therapy," *J Am Acad Dermatol,* (2000), 42:245–53.

Mjoo MD., Spuls Pl., Bos JD., Westerhof W., et al., "Nonsurgical repigmentation therapies in vitiligo," *Arch Dermatol,* (1998), 134:1532–40.

Njoo MD., Westerhof W., Bos JD., Bossuyt PM., "The development of guidelines for the treatment of vitiligo," *Arch Dermatol,* (1999), 135, 1514–21.

Ohshiro T., "Laser treatment of vitiligo" *Amer Society of Laser Med. And Surgery Abstracts,* 123:98.

Ortonne J., "Psoralen therapy in vitiligo," *Clin Dermatol,* (1989), 7:120–35.

Preston DS., Stern RS., "Nonmelanoma cancers of the skin," *N Engl J Med,* (1992), 327:1649–62.

Sasaki K., Ohshiro T., "Role of low reactive–level laser therapy (LLLT) in the treatment of acquired and cicatrical vitiligo," *Laser Therapy,* (1989), 1:141–146.

Stern RS., Lang R., "Non–melanoma skin cancer occurring in patients treated with PUVA five to ten years after first treatment," *J Invest Dermatol,* (1988),91:120–4.

Thissen, M., MD and Westerhof, W., MD, "Laser Treatment for further depigmentation in vitiligo," *Pharmacology and Therapeutics,* (1997), 36: 386–3388.

Westerhof W., Nieuweboer–Krobotova L,. "Treatment of Vitiligo with UV–B radiation vs Topical psoralen plus UV–A," *Arch Dermatol* (1997), 133:1525–28.

Yu H., Wu M., Kao Y., Wu C., "Helium–neon laser treatment induces repigmentation in segmental–type vitiligo," *Journ of Invest Dermatol* Abstracts 526.

Lotti, T.M., Menchini G., Andreassi L. UV–B radiation microphototherapy. An elective treatment for segmental vitiligo. J. Eur. Acad. Dermatol Venereol; 1999, 13(2):102–8.

Elliott J., "Clinical Experiences With Methosxalen In The Treatment Of Vitiligo", *J. Invest Dermatol.,* 1959; 32:311–14.

Farah F. et al., "The Treatment Of Vitiligo With Psoralens and Triamcinolone By Mouth", *Br. J. Dermatol.,* 1967; 79:89–91.

Ortonne J., "Psoralen Therapy In Vitiligo", *Clin. Dermatol.,* 1989; 7:120–35.

Stern, R.S. et al., "Non–melanoma Skin Cancer Occurring In Patients Treated With PUVA Five To Ten Years After First Treatment"; *J. Invest. Dermatol.,* 1988; 91:120–4.

Preston, D.S. et al., "Nonmelanoma Cancers Of The Skin", *N Engl. J. Med.,* 1992; 327:1649–62.

Westerhof W. et al., "Treatment Of Vitiligo With UV–B Radiation vs. Topical Psoralen Plus UV–A", *Arch Dermatol,* 1997; 133:1525–28.

Njoo, M.D. et al., "Treatment Of Generalized Vitiligo In Children With Narrow–Band (TL–01) UVB Radiation Therapy"; *J. Am. Acad. Dermatol.,* 2000; 42:245–53.

Njoo, M.D. et al., "Nonsurgical Repigmentation Therapies In Vitiligo", *Arch Dermatol.,* 1998; 134:1532–40.

Asawanonda, P. et al., "308–nm Excimer Laser For The Treatment of Psoriasis. A Dose Response Study", *Arch Dermatol.* 2000; 136:619–624.

Njoo, M.D. et al., "The Development Of Guidelines For The Treatment Of Vitiligo", *Arch Dermatol.* , 1999; 135:1514–21.

\* cited by examiner

TREATMENT OF VITILIGO

This application claims priority under 35 U.S.C. § 119 from the Provisional Application Ser. No. 60/184,971 filed Feb. 25, 2000, incorporated herein by reference in its entirety.

BACKGROUND OF THE INVENTION

Vitiligo is a cutaneous disease in which there is a complete loss of pigment in localized areas of the skin. This loss of pigment results in the effected areas being completely white. This condition has a predilection for the skin around the mouth and the eyes. The result is cosmetically disfiguring, especially for dark skinned people. Furthermore, the depigmented skin is sun sensitive, and thus is subject to sunburns and skin cancer. In sum, vitiligo is both cosmetically and practically distressing to patients afflicted with the disease.

In normal skin, varying shades of brown are seen (depending on a person's race) representing the pigment melanin. This pigment is produced by a cell type known as a melanocyte. In vitiligo, there is an absence of melanocytes in the areas afflicted with the disorder. An absence of melanocytes results in an absence of melanin pigment, and thus the melanin-free area is white. Normal skin responds to ultraviolet light with an increase in the brown pigment melanin (tanning). Specifically, ultraviolet radiation stimulates melanocytes to proliferate and produce more melanin.

Attempts have also been made to "tan" vitiligo areas using ultraviolet light treatments. The ultraviolet spectrum is divided into two portions, "UVA" and "UVB," which is light of 320–400 nm and 290–320 nm in wavelength, respectively. UVB is much more effective at producing a tan in normal skin. In normal skin, melanocytes reside in the epidermis, which is the outer layer of the skin. The epidermis is only 0.1 mm thick, so the melanocytes are very near the surface. UVB radiation can only penetrate to about 0.1 mm, but this is sufficient to reach the melanocytes. In patients with vitiligo, these epidermal melanocytes are gone. In some cases, there are surviving melanocytes deeper in the skin down the hair follicles. These melanocytes may be several millimeters deep. UVB cannot penetrate this deep in the skin to stimulate these surviving deep melanocytes. Exposure to UVB results in a sunburn at the surface of the skin with no stimulation of these deep melanocytes. Thus attempts to repopulate the vitiligo areas with melanocytes deep in the skin in response to UVB exposure have failed. UVA will penetrate a bit deeper in the skin than UVB. However, UVA is very poor at stimulating melanocytes to proliferate and migrate.

DESCRIPTION OF RELATED ART

The present invention uses an excimer laser to restore pigmentation to skin areas afflicted with vitiligo, and is an improvement over current treatments for vitiligo. Currently, treatments for vitiligo suffer from a number of drawbacks. For instance, Fitzpatrick's Dermatology in General Medicine, Vol. 1, Chapter 89 (5th ed., I. M. Freedberg et al., eds., 1999) teaches the use of sunscreens and cosmetic cover-ups including dyes and conventional makeup as a way to mask skin areas afflicted with vitiligo. However, the ability of sunscreens to minimize contrast between normal skin and vitiligo-afflicted areas has been disappointing. Sunscreens, as well as cosmetics and dyes, are not permanent. These products tend to rub-off and have been of limited value in areas such as the lower neck, wrists and hands. In addition, unlike the present invention, sunscreens and cosmetics cover-ups do not attempt to treat vitiligo, but simply blend in the affected areas with the surrounding skin. The prior art also teaches the use of topical glucocortoids to treat isolated areas of vitiligo. Fitzpatrick's Dermatology in General Medicine. However, the overall results tend to be disappointing. The present invention improves on these treatments by providing a more permanent restoration of pigmentation to vitiligo affected areas, with a relatively high rate of success.

Another known treatment for vitiligo attempts to increase the action of UVA light by combining exposure to UVA with a chemical that is applied to the skin to increase sensitivity to UVA. Fitzpatrick's Dermatology in General Medicine, Vol. 1, Chapter 89 (5th ed., I. M. Freedberg et al., eds., 1999). This chemical is known as psoralen, and psoralen and UVA together are known as PUVA. Specifically, high output UVA (320–400 nm) light bulbs are utilized within an indoor phototherapy unit. The patient applies psoralen to the effected areas, then stands inside the phototherapy unit for exposure to the UVA light emitted by conventional tube-style bulbs.

This type of PUVA treatment suffers from a number of drawbacks. Unlike the present invention, PUVA treatment is to the whole body, not just the vitiligo areas. Therefore PUVA therapy has been associated with the development of skin cancers. PUVA treatment is also time-consuming; a minimum of 100 treatments, given 2–3 times per week over many months, is necessary before any response is seen. In addition, this treatment has had a relatively low success rate. Significantly less than 50% of patients will respond to this treatment. The present invention, however, treats only those skin areas afflicted with vitiligo, and thus minimizes the risk of skin cancer. The present invention also is less time consuming, and enjoys a relatively higher success rate.

Topical PUVA also may be used to treat localized patches of vitiligo and consists of applying a topical preparation of 8-methoxypsoralen to the patch of vitiligo and exposing the patch to UVA radiation at intervals of two to three times weekly. This type of PUVA treatment also has a number of drawbacks. Erythema, blistering and hyperpigmentation of surrounding skin are common complications. In addition, the success rate is relatively low. Repigmentation is seen in only about half of treated patients. Westernof, W., et al., "Treatment of Vitiligo with UV-B Radiation vs. Topical Psoralen Plus UV-A," Arch. Dermatol; 1997; 133:1525–28.

Phototherapy with UV-A radiation and oral psoralens is another known treatment. UV-A irradiation occurs at intervals of two to three times weekly and is generally maintained for months to greater than a year. Once again, the success rate is relatively low. Elliott, J., "Clinical Experiences With Methosaxalen in the Treatment of Vitiligo", J. Invest Dermatol; 1959; 32: 311–314; Farah, F. et al, "The Treatment of Vitiligo with Psoralens and Triamcinolone By Mouth", Br. J. Dermatol; 1969; 79: 89–91; Ortonne J., "Psoralen Theraphy In Vitiligo", Clin. Dermatol; 1989; 7:120–135. Moreover, side effects of this type of PUVA include burning, nausea, erythema, lentigenes, pruritus, and cataracts.

UVB phototherapy is much more effective at stimulating melanocytes than PUVA. However, regular UVB light cannot penetrate the skin deeper than the epidermis, and hence is completely ineffective in stimulating the deep melanocytes underneath patches of vitiligo. The present invention overcomes this problem in the prior art through the use of an excimer laser which emits laser light in the ultraviolet range and provides higher energy fluences thereby decreasing the treatment time.

M. Thissen et al., Laser Treatment for Further Depigmentation in Vitiligo, International Journal of Dermatology, Vol. 36 (1997) teaches the use of a ruby laser to depigment normal skin and bleach it to a white color. Ruby lasers, unlike excimer lasers, employ a ruby crystal to generate laser light in the red spectrum. The laser light is used to depigment normal skin, and does not attempt to restore or treat skin areas afflicted by vitiligo. Therefore, unlike the present invention which attempts to stimulate melanin production and restore pigmentation, patients subjected to the Thissen treatment end up depigmenting their remaining normal skin. The drawbacks of this treatment are that the depigmented skin lacks melanin and is the color white, which is generally less aesthetically desirable than the natural skin color of the patient. This depigmented skin is also more sensitive to the sun than normally pigmented skin, and the patient with depigmented skin must be protected from the sun for the rest of his or her life. Finally, the Thissen article acknowledges that this method is only effective in vitiligo afflicted patients where the skin has become over 80% depigmented.

K. Sasaki et al., Role of Low Reactive-Level Laser Therapy (LLLT) in the Treatment of Acquired and Cicatrical Vitiligo, Laser Therapy, Vol. 1 No. 3 (1989) teaches use of a diode laser, either alone or in combination with an argon laser, to revive dormant or malfunctioning melanocytes in order to repigment vitiligo afflicted skin areas. This technique suffers from the disadvantage that both the argon and diode lasers are needed in order to treat cicatrical-type vitiligo, or vitiligo that follows after scarring or trauma. Argon lasers also suffer from the disadvantage that they may cause thermal damage to the skin. In addition, argon lasers as disclosed in Sasaki emit visible light (488 nm and 514.5 nm), while diode lasers emit infrared light (830 nm). Unlike the present invention, these lasers do not emit UV light, and therefore do not benefit from the special ability UVB light has in stimulating melanocyte growth and melanin production.

H. Yu et al., Helium-Neon Laser Treatment Induces Repigmentation in Segmental-Type Vitiligo, Journal of Investigative Dermatology, Vol. 112(4) (1999) teaches use of a Helium-Neon laser that emits light in the visible red to infrared range, as opposed to UV light. Unlike the present invention, Helium-Neon laser light suffers from the disadvantage that it does not stimulate melanocytes directly, but instead induces nerve growth. For this reason, this method of treating vitiligo is confined to segmental-type vitiligo, which is vitiligo caused by dysfunction of nerves.

Lasers have also been used to treat vitiligo to aid in skin grafting. R. Kaufman, et al., Grafting of In Vitro Cultured Melanocytes onto Laser-Ablated Lesions in Vitiligo, ACTA Demato-Veneriologica, Vol. 78/2 (1998); J. S. Yang et al., Treatment of Vitiligo with Autologous Epidermal Grafting by Means of Pulsed Erbium:YAB Laser, Journal of the American Academy of Dermatology, Vol. 38/2 (1998). Unlike the present invention, these techniques are invasive and require that the vitiligo affected areas be relatively small and stable.

Narrowband UV-B phototherapy using a spectrum of 311–315 nm wavelength with a peak emission of 311 nm has been used to treat vitiligo. Westerhof et al. teaches the use of narrowband UV-B phototherapy at intervals of two times per week for four to twelve months. However, this method requires regular phototherapy sessions several times a week for up to a year to achieve a therapeutic response. UV-B phototherapy in general has few side effects and is mainly limited to erythema.

What is needed is a method of treating vitiligo with UVB light that treats only the areas of vitiligo with increased precision, at higher energy fluences, to reduce length of treatment. What is also needed is a method of treating vitiligo that is as effective as UVB light in stimulating melanocytes, but without the disadvantage of being unable to penetrate beyond the epidermal skin layer. What is also needed is a method of treating vitiligo that only treats the areas of the vitiligo, and not the entire body, to reduce the risk of skin cancers. Finally, what is needed is a method that restores pigmentation to skin areas afflicted with vitiligo, rather than simply covering the affected areas or bleaching normal skin white, so that the result is both more permanent and more aesthetically pleasing.

BRIEF SUMMARY OF THE INVENTION

The present invention is a method of treating vitiligo using an excimer laser, a laser which produces light in the UVB range. The present invention includes a method for treating vitiligo by incrementally increasing exposure of afflicted areas of skin with UVB laser light to restore the pigmentation in the areas afflicted with vitiligo. The present invention overcomes the problems associated with current vitiligo treatments through the use of an excimer laser. Laser light is coherent and collimated whereas regular light is incoherent and divergent, allowing laser UVB light to penetrate deeper into skin and quickly stimulate deep melanocytes underneath patches of vitiligo. Therefore unlike regular UVB light or, PUVA therapy, the present invention is able to better stimulate deep melanocytes, and is able to deliver higher energy fluences in less time than known treatments. Another advantage of the present invention is that laser treatment is confined to only those areas afflicted with vitiligo, not to normal skin, and thus significantly reduces risk of skin cancers over other types of therapy such as PUVA treatments. Yet another advantage of the present invention is that the vitiligo areas are treated and made darker, making the areas better match the natural skin color of the patient, as opposed to simply bleaching the surrounding non-vitiligo areas to an unnatural white. Finally, the present invention changes the actual pigment of the skin, and therefore will not rub or wash-off.

(A) BRIEF DESCRIPTION OF THE DRAWINGS

The patent or application file contains at least one drawing executed in color. Copies of this patent or patent application publication with color drawing(s) will be provided by the Office upon request and payment of the necessary fee.

(B) DETAILED DESCRIPTION OF THE INVENTION

Figure 1:
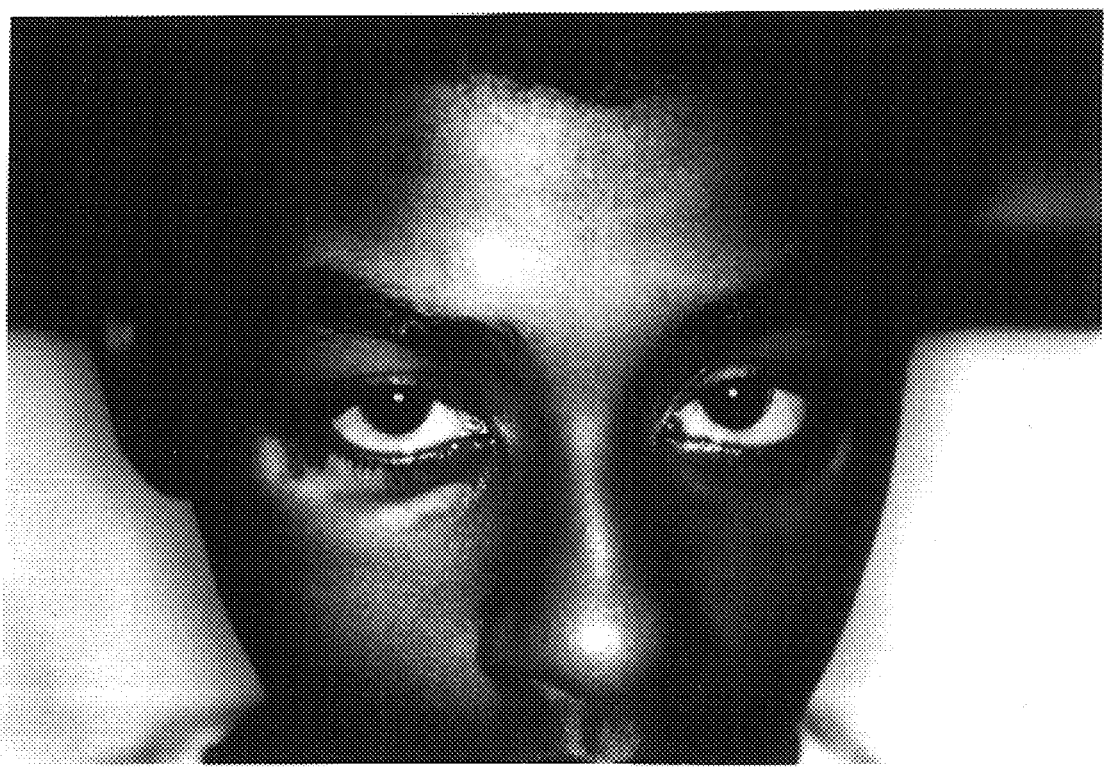
FIG. 1 depicts vitiligo involving periocular skin in an individual with phototype V skin before treatment.
Figure 2:
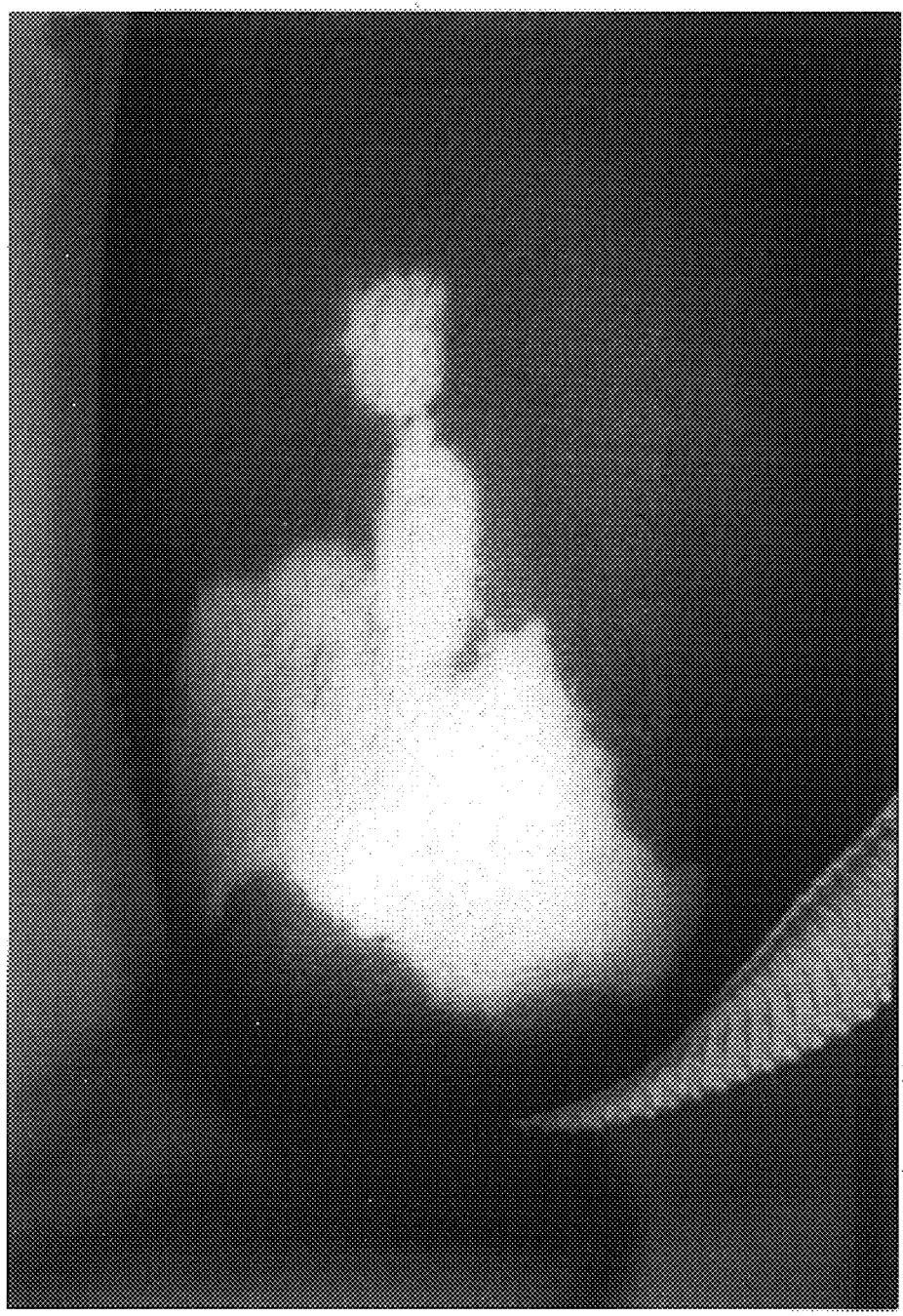
FIG. 2 depicts vitiligo involving the extensor elbow in an individual with phototype V skin before treatment.
Figure 3:
FIG. 3 depicts vitiligo involving the periocular skin in an individual with phototype III skin before treatment.

The present invention is a method of using UVB laser light to treat vitiligo. Laser light is different than regular light in that it is coherent and collimated, which can be thought of as more "concentrated." A given dose of laser light is often much more effective in producing photochemical reactions than conventional light. Treatment of vitiligo with UVB laser light is superior because laser light 1) penetrates deeper in the skin than conventional light, and 2) a given dose of light is delivered much more quickly with laser light. This second effect becomes important if stimulation of melanocytes has a time component, i.e. stimulation is more effective if done quickly.

Also claimed and disclosed is a method of using UVB laser light to treat vitiligo where the time of exposure to the vitiligo afflicted skin areas is gradually increased. A diagnosis of vitiligo is made clinically, and the absence of melanin is confirmed by Woods light examination. A Wood's light examination uses UV light, also known as "black light," to accentuate areas of white color. In the practicing invention, a patient afflicted with vitiligo is treated by exposing the afflicted area to the UVB laser beam at periodic intervals. For example, the exposure to the vitiligo afflicted skin areas can be administered between 1 to 5 times per week. The first treatment would last for up to 5 seconds, depending on the intensity setting of the laser beam. The greater the intensity, the shorter the exposure to the beam. The exposure time for each treatment would be gradually increased, to a maximum of 10 seconds.

In one embodiment of the invention, an excimer laser is used to generate the UVB laser light. An excimer laser is a laser which uses a rare-gas halide or rare-gas metal vapor and emits laser light in the ultraviolet (126 to 558 nm) range. Currently, only excimer lasers emit laser light in the UV range, although any future lasers that emit light in the UVB range would also be encompassed by this invention. The laser used should operate in a range between 290 and 320 nm in wavelength, the UVB range of light. The laser should be utilized at a setting of not more than 120 mwatts.

A 308 excimer laser from the Surgilight Corporation, Winter Park Fla., is preferred for use in practicing the present invention. This laser operates at 308 nm via a fiber optic cable with pulse duration of 120 nsec, fired at repetition rate of 20 hz. The laser spot size is 10×10 mm. A photometer measures laser output, and the laser is utilized at a setting of 60 mwatts. In one preferred method of treatment, a patient with vitiligo is exposed to the 308 nm excimer laser three times a week. The first treatment lasts 2 seconds. The patient returns, and if there is no sunburn, the treated area is retreated again for 2 seconds. If there is sunburn, treatment is withheld until the sunburn is gone. On the third visit, if there is no sunburn, the dose is increased to 4 seconds. This is repeated the fourth visit, and then increased to 6 seconds on the fifth visit. On the sixth visit, 6 seconds is given again. Therefore, in this preferred method, each dose is repeated once, then increased by two seconds, to a maximum of 10 seconds. Treatment is continued for one month, or until repigmentation occurs, which is a much shorter time than PUVA therapy, which typically takes 6 months before any result is seen. Repigmentation is the appearance of brown pigment in the treated area, and is documented by standardized photography. In preliminary trials, four out of five patients receiving treatment for a minimum of nine sessions showed some response. This is a significant and substantial improvement in success rate over PUVA, glucocortoids, or any other current therapy for vitiligo. The repigmented skin is also relatively more permanent than other treatments such as sunscreens and cosmetic cover-ups, and will not rub-off.

When compared to standard phototheraphy, the 308 nm excimer laser has the advantage of having increased precision and the ability to deliver higher energy fluences thereby decreasing treatment time.

EXAMPLES

The following are intended as non-limiting examples of the invention.

Six men and twelve women with multiple discreet chronic stable patches of vitiligo enrolled in the study. Most patients had received and failed a variety of prior therapies for vitiligo (Table 1). No patient received any additional vitiligo therapy for at least one month prior to and during the study.

Eighteen patients started the study with a total of twenty-nine treated vitiligo patches. All patients had untreated vitiligo patches that were used as controls. Test areas of vitiligo were treated using a 308-nm xenon chloride excimer laser. A 120-ns, 20-hz, pulse was used with a 10-mm by 10-mm spot size and a power output of 60 mw of laser light. Lesions were treated three times a week for a maximum of 12 treatments. Exposure time was started at 2 seconds and increased by 2 seconds at every other visit until complete repigmentation occurred or until the protocol (12 treatments) was completed. Treatment was withheld if sunburn was observed and held until resolution.

Treated areas were evaluated for repigmentation and erythema on separate four point scales. Repigmentation was graded on the percentage of treated area of repigmentation as follows: 0:0%, 1:1–25%, 2:26–75% and 3:76–100%. Sunburn (erythema) was similarly graded as follows: 0—None, 1—Mild, 2—Moderate, 3—Severe. Patients with no repigmentation were defined as non-responders.

Results

Figure 4:
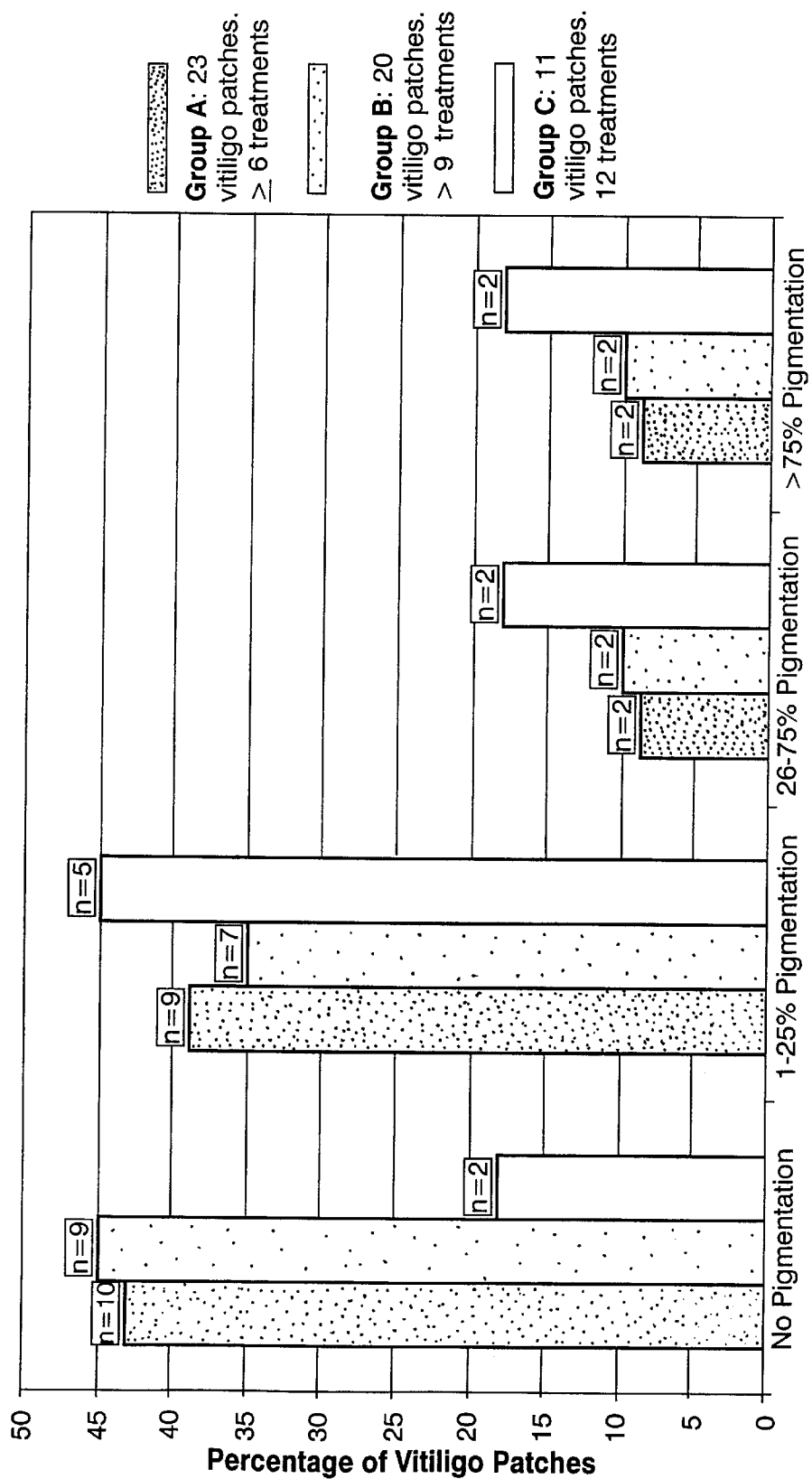
FIG. 4 depicts a comparison of the number of treatments and the degree of repigmentation in the study population.
Figure 5:
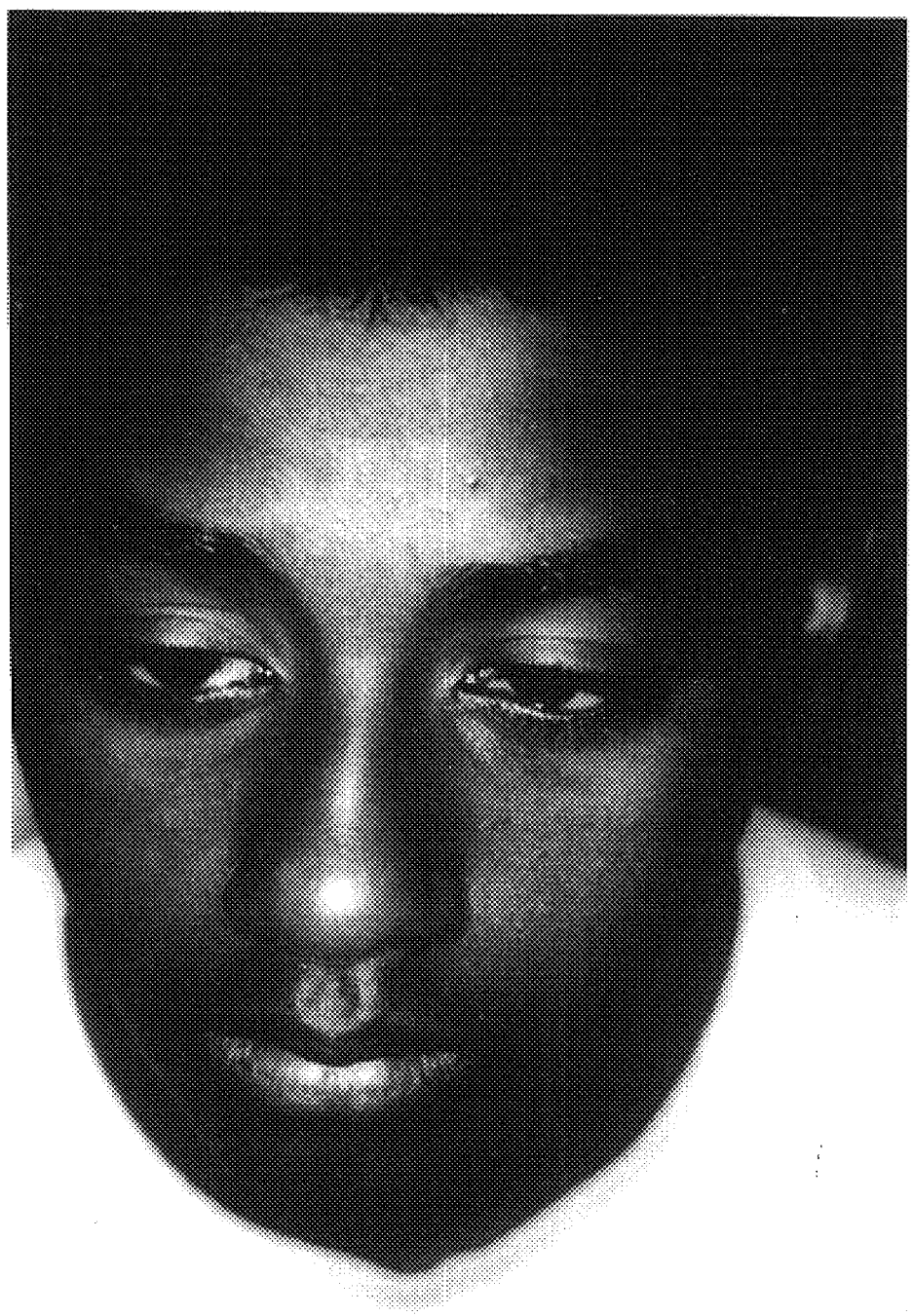
FIG. 5 depicts complete repigmentation of the vitiligo-affected periocular skin shown in FIG. 1 after 5 treatments.
Figure 6:
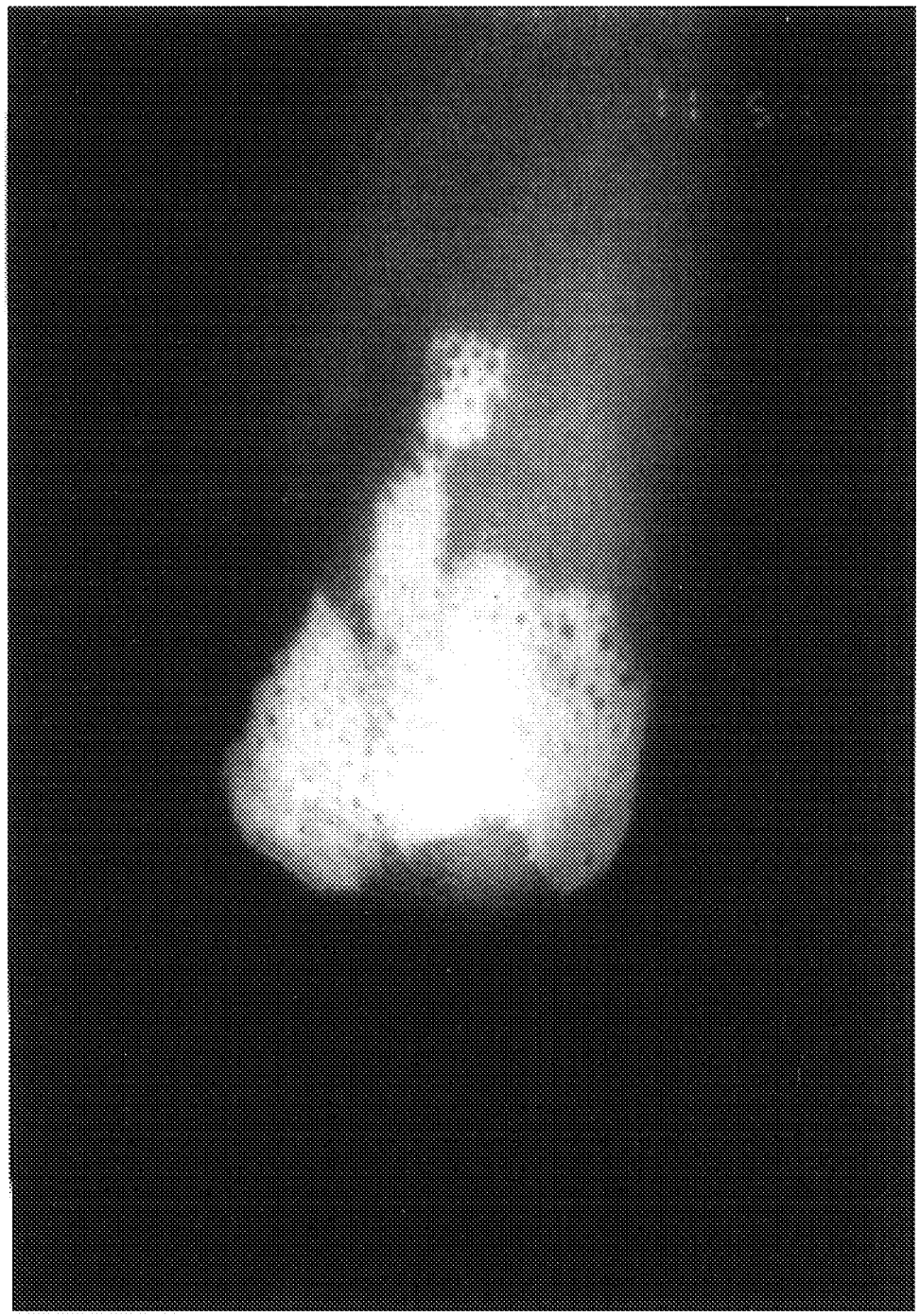
FIG. 6 depicts spotty follicular repigmentation of the vitiligo-affected extensor elbow shown in FIG. 2 after 12 treatments.
Figure 7:
FIG. 7 depicts focal repigmentation of the vitiligo-affected periocular skin shown in FIG. 3 after 12 treatments.

Twelve patients with 23 patches completed at least six treatments. Six patients with 11 patches of vitiligo completed all twelve treatments that required an average of four weeks to complete. Six patients dropped out of the study before completion of six treatments and resulted in one slight repigmentation and five non-responders. Two of the non-responders developed mild erythema. Twelve patients with six or more total treatments of 23 vitiligo patches resulted in partial repigmentation in 57% of twenty-three patches. Six patients who completed twelve treatments of 11 vitiligo patches resulted in partial repigmentation in 87% of eleven patches (FIG. 4). There were no serious adverse events. Mild sunburn with persistent erythema lasting up to three weeks was observed in some patients. Patients with the most repigmentation were skin-types III–VI. Table 1 sets forth the results.

TABLE 1

Demographics and Study Results of Patients Involved In the Protocol

| Patient | Sex | Skin Phototype | Prior Treatment | Treatment Locations | Treatments Received | % Repigmentation* | Erythema** |
|---|---|---|---|---|---|---|---|
| 1 | M | V | TS | Periocular | 5 | 3 | 0 |
|   |   |   |    | Forearm | 12 | 3 | 0 |
| 2 | F | III | PUVA | Periocular | 12 | 1 | 0 |
|   |   |   |    | Back | 12 | 1 | 0 |
|   |   |   |    | Hand | 12 | 0 | 0 |
|   |   |   |    | Thigh | 12 | 1 | 0 |
| 3 | F | I | None | L. Forearm | 12 | 1 | 1 |
| 4 | F | III–IV | None | L. Preauricular | 9 |   |   |
| 5 | M | II | None | L. Neck | 3 | 0 | 1 |
| 6 | F | II | TS. Folate | L. Hand | 5 | 1 | 0 |
| 7 | F | IV | PUVA | Finger | 12 | 0 | 0 |
| 8 | M | II | TS | Abdomen | 3 | 0 | 1 |
| 9 | F | VI | TS | R. Temple | 2 | 0 | 0 |
| 10 | F | II | None | R. Wrist | 6 |   |   |
| 11 | F | III–IV | None | R. Axilla | 8 | 1 | 1 |
|   |   |   |    | Sternum | 8 | 1 | 1 |
| 12 | F |   | None | R. Axilla | 1 | 0 | 0 |
| 13 | M | III–IV | None | Chin | 10 | 0 | 1 |
|   |   |   |    | L. Elbow | 10 | 0 | 1 |
|   |   |   |    | L. Arm | 10 | 0 | 1 |
| 14 | M | II | PUVA | L. periocular | 10 | 0 | 1 |
|   |   |   |    | R. Elbow | 10 | 1 | 0 |
|   |   |   |    | Chin | 10 | 0 | 1 |
| 15 | F | II | PUVA | L. Shin | 9 | 1 | 0 |
|   |   |   |    | L. Elbow | 9 | 0 | 1 |
| 16 | F | II | TS | Forearm | 5 | 0 | 0 |
| 17 | M | IV | PUVA | Forehead | 12 | 1 | 0 |
|   |   |   |    | Chin | 12 | 1 | 0 |
| 18 | F | V | None | Elbow | 12 | 2 | 0 |

*Repigmentation: 0 = 0; 1 = 1–25%; 2 = 26–75%; 3 = 76–100%
**Erythema: 0 = none; 1 = mild; 2 = moderate; 3 = severe While the invention has been particularly shown and described with reference to preferred embodiments thereof, it will be understood by those skilled in the art that various changes in form and details may be made therein without departing from the spirit and scope of the invention. All patent applications, patents, patent publications and literature references cited in this specification are hereby incorporated by reference in their entirety.

What is claimed is:

1. A method of treating vitiligo comprising the steps of:
   (A) identifying an area of skin with an absence of melanin,
   (B) exposing said area of skin to laser light in the UVB range for 10 seconds or less, and
   (C) repeating said exposure until said skin is repigmented.

2. The method of claim 1 wherein the wavelength of said laser light is 308 nm, and the intensity of said laser light is 60 mwatts.

3. The method of claim 2 wherein said area of skin is exposed at least 3 times a week.

4. The method of claim 1 wherein the wavelength of said laser light is 290 to 320 nm.

5. The method of claim 4 wherein the intensity of said laser light is not more than 120 mwatts.

6. The method of claim 2 or 5 wherein said area of skin is exposed 1–5 times a week.

7. The method of claim 1 wherein each exposure of said area of skin to laser light occurs for an incrementally increased time period.

8. The method of claim 1 which comprises stimulating melanin production in said area of skin with said repeated exposures.

9. A method of treating vitiligo comprising the steps of;
   (A) identifying an area of skin with an absence of melanin,
   (B) first exposing said area of skin to UVB laser light for 1–5 seconds,
   (C) increasing the length of exposure of said area of skin by 1–3 seconds after every two exposures until said area of skin is repigmented.

10. The method of claim 9 wherein the UVB laser light is generated by an excimer laser.

11. The method of claim 10 wherein the wavelength of said laser light is 308 nm, and the intensity of said laser light is 60 mwats.

12. The method of claim 11 wherein said area of skin is exposed at least 3 times a week.

13. The method of claim 9 wherein the wavelength of said laser light is 290–320 nm.

14. The method of claim 13 wherein the intensity of said laser light is no more than 120 mwatts.

15. The method of claim 14 wherein said area of skin is exposed 1–5 times a week.

16. A method of treating vitiligo comprising the steps of:
   (A) identifying an area of skin with an absence of melanin,
   (B) repeatedly exposing said area of skin to excimer laser light having a wavelength of 308 nm and an intensity of 60 mwatts,
   (C) exposing said area of skin to said laser light 1–5 times a week for not more than 5 seconds during the first exposure; and
   (D)) gradually increasing the exposure time to a maximum of 10 seconds per exposure.

17. A method of treating vitiligo comprising the steps of;
(A) identifying an area of skin with an absence of melanin,
(B) repeatedly exposing said area of skin to laser light having a wavelength of 290 to 320 nm and an intensity not more than 120 mwatts,
(C) exposing said area of skin to said laser light 1–5 times a week for not more than 5 seconds during the first exposure; and
(D) gradually increasing the exposure time to a maximum of 10 seconds per exposure.

18. A method of treating vitiligo comprising the steps of;
(A) identifying an area of skin with an absence of melanin,
(B) repeatedly exposing said area of skin to excimer laser light having a wavelength of 308 nm and an intensity of 60 mwatts,
(C) exposing said area of skin at least 3 times a week for 2 seconds during the first exposure; and
(D) increasing the exposure time by 2 seconds after every two exposures.

19. A method of treating vitiligo comprising the steps of:
(A) identifying an area of skin with an absence of melanin,
(B) exposing said area of skin to laser light in the UVB range for between 1 and 5 seconds, and
(C) repeating said exposure until said skin is repigmented.

* * * * *